United States Patent
Wognum et al.

(10) Patent No.: US 9,273,285 B1
(45) Date of Patent: Mar. 1, 2016

(54) SHORTER COLONY-FORMING CELL ASSAY

(75) Inventors: Albertus W. Wognum, Vancouver (CA); Ning Yuan, Vancouver (CA)

(73) Assignee: STEMCELL TECHNOLOGIES INC., Vancouver (CA)

( * ) Notice: Subject to any disclaimer, the term of this patent is extended or adjusted under 35 U.S.C. 154(b) by 1139 days.

(21) Appl. No.: 12/547,052

(22) Filed: Aug. 25, 2009

Related U.S. Application Data (60) Provisional application No. 61/110,149, filed on Oct. 31, 2008, provisional application No. 61/091,524, filed on Aug. 25, 2008.

(51) Int. Cl.
 *G01N 33/567* (2006.01)
 *C12N 5/0789* (2010.01)
 *A61K 35/12* (2015.01)

(52) U.S. Cl.
 CPC .............. *C12N 5/0647* (2013.01); *A61K 35/12* (2013.01); *C12N 2501/145* (2013.01); *C12N 2501/26* (2013.01)

(58) Field of Classification Search
 CPC .................................................. G01N 33/567
 See application file for complete search history.

(56) References Cited

U.S. PATENT DOCUMENTS

| | | | |
|---|---|---|---|
| 6,962,698 B1 * | 11/2005 | Peled et al. ................... | 424/93.7 |
| 7,354,729 B2 | 4/2008 | Rich | |
| 7,989,178 B2 * | 8/2011 | Rich ................................ | 435/8 |
| 2002/0146680 A1 * | 10/2002 | Rich ................................ | 435/4 |
| 2007/0059778 A1 | 3/2007 | Wognum et al. | |

OTHER PUBLICATIONS

Prasad et al. (Unrelated donor umbilical cord clood transplantation for inherited metabolic disorders in 159 patients from a single center: influence of cellular composition of the graft on transplantation outcomes, Blood epub Jun. 27, 2008, vol. 112, p. 2979-2989.*
MacDonald et al., The Role of Zinc in Growth and Cell proliferation, Journal of Nutrition, vol. 130, p. 1500S-1508S, 2000.*
Murray et al., Thrombopoietin, flt3, and kit ligands together suppress apoptosis of human mobilized CD34 cells and recruit primitive CD34 Thy-1 cells into rapid division, Experimental Hematology, 1999, vol. 27, p. 1019-1028.*
Broxmeyer et al., Human umbilical cord blodd as a potential source of transplantable hematopoietic stem/progenitor cells, PNAS, 1989, vol. 86, p. 3828-3832.*
Qiu et al., Ex vivo expansion of CD34 umbilical cord blood cells in a defined serum-free medium (QBSF-60) with early effect cytokines, Journal of Hematotherapy & Stem cell Research, vol. 8, p. 609-618, 1999.*
Rich, I.N. and Hall, "Validation and Development of a Predictive Paradigm for Hemotoxicology Using a Multifunctional Bioluminescence Colony-Forming Proliferation Assay", Toxicological Sciences, 2005, pp. 427-441, vol. 87, No. 2.
Reems, J. et al., "Development of a novel assay to evaluate the functional potential of umbilical cord blood progenitors", Transfusion, 2008, pp. 620-628, vol. 48.
Rich, et al., "In vitro hematotoxicity testing in drug development: a review of past, present and future applications", Current Opinion in Drug Discovery & Development, 2003, pp. 100-109, vol. 6, No. 1.
Hemogenix (http://www.hemoqenix.com/replacinq_cfa_with_halo/). Printed Oct. 20, 2009, p. 17.
Rodgers, K.E., et al., "Effect of Angiotensin II on Hematopoietic Progenitor Cell Proliferation", Stem Cells, 2000, pp. 287-294, vol. 18.
Broxmeyer, H., et al., "Comparative analysis of the influences of human gamma, alpha and beta interferons on human multipotential (CFU-GEMM), erythroid (BFU-E) and granulocyte-macrophage (CFU-GM) progenitor cells", The Journal of Immunology, 1983, pp. 1300-1305, vol. 131, No. 3.
Ferrero, D. et al., "Antigenically distinct subpopulations of myeloid progenitor cells (CFU-GM) in human peripheral blood and marrow", Proc. Natl. Acad. Sci. USA, 1983, pp. 4114-4118, vol. 80.
Gregory, C.J. and Eaves, A.C., "Human marrow cells capable of erythropoietic differentiation in vitro: definition of three erythroid colony responses", Blood, 1977, pp. 855-864, vol. 49, No. 6.
Jacobsen, N., et al., "Diversity of human granulopoietic precursor cells: separation of cells that form colonies in diffusion chambers (CFU-d) from populations of colony-forming cells in vitro (CFU-c) by velocity sedimentation", Blood, 1978, pp. 221-232, vol. 52, No. 1.
Jacobsen, N., et al., Colony-forming units in diffusion chambers (CFU-d) and colony-forming units in agar culture (CFU-c) obtained from normal human bone marrow: a possible parent-progeny relationship, Cell Tissue Kinet., 1979, pp. 213-226, vol. 12.

* cited by examiner

*Primary Examiner* — Taeyoon Kim
*Assistant Examiner* — Tiffany Gough
(74) *Attorney, Agent, or Firm* — Bereskin & Parr LLP; Melanie Szweras (57) ABSTRACT

The present disclosure provides a method of determining the frequency and proliferative potential of progenitor cells in a starting cell preparation comprising (a) culturing the cell preparation for 5-10 days in a culture medium comprising FLT-3 Ligand (FL) and Thrombopoietin (TPO); (b) detecting and enumerating the colonies; and (c) assessing the frequency and proliferative potential of progenitor cells in the starting cell preparation based on the number of colonies in step (b). The number of colonies in step (b) correlates to the number of colonies in a standard 14-day colony-forming cell assay. The method is particularly useful for predicting and evaluating the suitability of grafts for transplantation.

18 Claims, 10 Drawing Sheets

SHORTER COLONY-FORMING CELL ASSAY

RELATED APPLICATIONS

This application claims the benefit under 35 USC §119(e) of U.S. provisional application No. 61/110,149 filed Oct. 31, 2008 and U.S. provisional application No. 61/091,524 filed Aug. 25, 2008, both of which are incorporated herein in their entirety.

FIELD OF THE DISCLOSURE

The disclosure relates to a method of improving colony-forming cell assays. In particular the method provides a shorter colony-forming cell assay than the standard assay and uses thereof.

BACKGROUND OF THE DISCLOSURE

In the adult, hematopoiesis is maintained by the constant regulated production of billions of mature blood cells derived from a small population of relatively quiescent hematopoietic stem cells (HSC) located in the bone marrow. These cells have the potential to undergo self-renewal to maintain their numbers and to produce cells of all the hematopoietic lineages. Proliferation and differentiation of HSC produces a heterogeneous compartment of actively dividing cells called hematopoietic progenitors. With progressive cell divisions, these progenitors have limited self-renewal capacity and become committed to the various blood cell lineages i.e. white blood cells, red blood cells and platelets.

Since their introduction more than 30 years ago, colony assays have been used extensively for research and clinical applications of hematopoietic cells in particular. These include identification of stimulatory and inhibitory growth factors, supportive diagnostic assays of myeloproliferative disorders and leukemias, and evaluation of the hematopoietic proliferative potential of bone marrow (BM), cord blood (CB) and mobilised peripheral blood (MPB) samples for clinical transplantation. Hematopoietic progenitor cells will proliferate and differentiate in vitro to produce distinct colonies in semi-solid media. Culture conditions that promote such colonies have been optimised and standardised offering a reproducible functional assay for hematopoietic progenitors. This assay has been called the colony forming cell (CFC) assay. The CFC assay has become the benchmark functional assay to assess the ability of various hematopoietic cell sources to divide and differentiate, especially following ex vivo manipulations including T-cell depletion, $CD34^+$ cell enrichment, gene therapy protocols and cryopreservation. The CFC assay is also used to screen novel drug candidates for potential toxicity on hematopoietic cells.

Hematopoietic CFC assays are used to quantify multi-potential progenitors and single lineage restricted progenitors of the erythroid, granulocytic, monocyte-macrophage and megakaryocytic pathways. The most commonly used procedure involves the plating of a single cell suspension into semi-solid nutrient medium supplemented with the appropriate combinations of cytokines that supports the proliferation and differentiation of individual progenitor cells into discrete colonies containing recognizable progeny. The CFCs are classified and enumerated based on morphologic recognition of mature cells within the colony in situ by light microscopy. The number of colonies obtained should be linearly proportional to CFC content of the input cell suspension provided that a sufficiently low number of cells are plated. In general, under 'optimal' assay conditions, colonies containing cells of two or more lineages (mixed colonies) arise from a more primitive progenitor than those containing cells of a single lineage. In addition, more immature progenitors generate larger colonies and require a longer period of time in culture to allow maturation of the cells within the colony.

Colony identification on the basis of size and morphology is inherently subjective and there can be considerable variation in the determination of absolute CFC (Bacigalupo et al. Bone Marrow Transplantation (1995); Torres et al. Blut (1985)). Inconsistent scoring can result from differences in the criteria for colony identification between groups and inexperience of laboratory personnel (Burger et al., Transfusion (1999); Lumley et al. Bone Marrow Transplantation (1999); Lamana et al., Bone Marrow Transplantation (1999)). When training new personnel, comparative counting with experienced staff provides the most useful form of instruction and should be continued until an adequate level of proficiency is attained. Even for accomplished staff, cross-comparisons once a month of counts with common set of progenitor cultures is recommended to maintain reproducible scoring. In addition, different types of colonies can only be counted at the end of a lengthy culture period, typically 14-16 days, when colonies have sufficiently matured.

SUMMARY OF THE DISCLOSURE

The present inventors have developed a modified colony-forming cell assay where individual colonies can be identified at earlier time points during culture.

Accordingly, the application provides a method of determining the frequency and proliferative potential of progenitor cells in a starting cell preparation comprising:

a) culturing the cell preparation for 5-10 days in a culture medium comprising FLT-3 Ligand (FL) and Thrombopoietin (TPO);

b) detecting and enumerating the colonies; and c) assessing the frequency and proliferative potential of progenitor cells in the starting cell preparation based on the number of colonies in step (b); wherein the number of colonies in step (b) is correlated to the number of colonies in a standard 14-day colony-forming cell assay.

In one embodiment, the culture period is from 6-8 days, such as 7 days. In another embodiment, the culture medium is modified to permit acceleration of the proliferation of progenitors. In yet another embodiment, the development of colonies is accelerated by using further cytokines or other culture supplements that promote the proliferation of progenitor cells and/or inhibit or delay their differentiation, irrespective of the type of progenitor cell. In a further embodiment, the culture medium is supplemented with zinc ions to promote the number and size of colonies to facilitate their detection and enumeration as early as after 5 days of culture.

In yet another aspect, the present application provides a method of predicting or evaluating the quality of a hematopoietic graft comprising predicting the proliferative potential of progenitor cells of a starting cell preparation derived from the hematopoietic graft using the methods described herein. In one embodiment, the graft is allogeneic, xenogeneic, syngeneic or autologous to a subject in need thereof.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION OF THE DISCLOSURE

The present inventors have developed modifications to the standard colony-forming cell (CFC) assay that enable earlier and more consistent enumeration of colonies that are representative of the progenitor numbers present in the original cell preparation. Although distinction between colony types on the basis of differences in morphology or degree of hemoglobinization is not possible as the cells have not been sufficiently matured to be morphologically distinguishable, for some applications distinction between colony types is less important than the ability to count colonies after a shorter culture period.

Accordingly, in one aspect, the disclosure provides a method of determining the frequency and proliferative potential of progenitor cells in a starting cell preparation comprising:

a) culturing the cell preparation for 5-10 days in a culture medium comprising FLT-3 Ligand (FL) and Thrombopoietin (TPO);

b) detecting and enumerating the colonies; and c) assessing the frequency and proliferative potential of progenitor cells in the starting cell preparation based on the number of colonies in step (b); wherein the number of colonies in step (b) is correlated to the number of colonies in a standard 14-day colony-forming cell assay.

In one embodiment, the culture period is from 6 to 8 days. In a further embodiment, the culture period is 7 days.

The term "proliferative potential" as used herein refers to the cell growth ability of the starting cell preparation and correlates with the number of colonies detected in the colony forming cell assay. For example, a larger number of colonies correlates with a higher progenitor frequency and better ability of the starting cell preparation to engraft after transplantation. The number of colonies is normalized based on the amount of cells initially cultured, but for transplantation purposes it can also be expressed relative to the body weight of the recipient of the graft. A colony number of greater than $5.6 \times 10^4$ per kg body weight is considered a good proliferative potential.

The phrase "the number of colonies in step (b) is correlated to the number of colonies in a standard 14-day colony-forming cell assay" as used herein refers to a significant correlation of the number of colonies enumerated at the shorter culture time period and the number of colonies enumerated at a standard 14-day culture period under the same culture conditions. For example, the number of colonies at step (b) is at least 70%, at least 75%, at least 80%, at least 85%, or at least 90% of the number of colonies that would be present in a standard 14-day CFC assay under the same culture conditions.

The cell preparation is cultured in a culture medium that is suitable for the growth of the progenitor cells. The cell culture medium can be any medium that can support the growth of cells including, without limitation, a semi-solid medium. The most widely used media formulations contain 0.8-1.0% methylcellulose as the semi-solid matrix, fetal bovine serum (FBS), bovine serum albumin (BSA) and recombinant cytokines. Less widely used are CFC assays that contain agar or collagen as the semisolid matrix. Accordingly, in one embodiment, the culture medium is a semi-solid medium, such as a methylcellulose, agar, collagen or plasma clot based culture medium. In another embodiment, the culture medium is methylcellulose based.

The starting cell preparation can be obtained from cells or tissue from any source including but not limited to embryonic, post-natal or adult tissue. Further, the cells may be obtained from normal or tumor tissue. The starting cell preparation can be any cell preparation comprising progenitor cells, including but not limited to hematopoietic tissues, such as blood, bone marrow, cord blood, placenta, spleen, fetal liver, yolk sac, or aorta-gonad-mesonephros region. Non-hematopoietic tissues include, without limitation, cultured embryonic stem cell lines or induced pluripotent stem cell lines derived from any tissue. In one embodiment, the starting cell preparation is bone marrow, cord blood or mobilized peripheral blood samples. In another embodiment, the starting cell preparation has been cryopreserved.

The term "hematopoietic progenitor cell" as used herein refers to an actively dividing cell with limited self-renewal capacity, committed to producing cells of one or several blood cell lineages, including, without limitation, white blood cells, red blood cells and platelets.

The term "colony" as used herein refers to the cells grown in the culture medium that fulfill the traditional characteristic colony forming unit description of a cell cluster or a group of cell clusters with a minimum of 20 cells per colony and originating from a single progenitor cell.

The term "detecting" as used herein means identifying colonies in situ, for example, by light or fluorescent microscopy. The term "enumerating" as used herein means counting the number of colonies grown. The CFCs are classified and enumerated based on morphologic recognition of mature cells within the colony. For example, colony enumeration can be performed using a quality inverted microscope for detection of colonies in methylcellulose-based cultures. An inverted microscope equipped with 10 or 12.5 times eyepiece objectives and planar objectives 2 times, 4 times and 10 times is recommended. The colonies are identified based on size and if differentiated, based on morphological characteristics.

Automation of colony detection and counting would eliminate variability due to observer subjectivity and inexperience, and thus increase consistency and reproducibility of the CFC assay. Accordingly, in one embodiment, enumeration is performed using an automated colony detection instrument. Examples include, without limitation, the Cellavista image based platform from Innovatis AG (Germany), the Gelcount mammalian Cell Colony counter from Oxford Optronix (UK), the Isocyte laser scanning cytometer from Blueshift Biotechnologies (USA) and similar instruments from Cellomics, GE Healthcare and Molecular Devices.

Colony detection, in particular by automated systems, can be facilitated by the use of cell labeling and detection reagents, as described in US-patent application 2007/0059778, incorporated herein by reference. The cell labeling and detection reagent can be any reagent that can detect the progenitor cell or specific cell types. In one embodiment, the detection reagents are antibodies that are specific to cell types present in the colonies after 5-10 days of culture. Preferentially, these antibodies are labeled with fluorescent molecules, e.g., fluorescein, thus enabling colony detection by fluorescence microscopy. This increases the ability to accurately identify and enumerate colonies.

Conjugated antibodies against the cell-surface antigens CD34 and CD45 can be used to detect colonies after reduced culture periods as these antibodies can stain colonies that contain immature hematopoietic cells, which are all CD45+ and may express CD34. Conjugated antibodies against antigens expressed on mature macrophages and granulocytes, e.g., CD11b, and against antigens expressed on erythroid cells e.g, Glycophorin-A, are less useful as most cells in colonies after reduced culture periods are still undifferentiated and either do not express these antigens or express them at lower levels than on differentiated cells.

In another embodiment, cell labeling and detection reagents are compounds that react with a cellular component. Examples include, without limitation, tetrazolium compounds such as (3-(4,5-Dimethylthiazol-2-yl)-2,5-diphenyltetrazolium bromide (Yellow MTT), MitoTracker Green FM, MitoTracker Deep Red 633, Hoechst 33342, calcein AM, calcein red-orange AM, Lavacell (Active Motif, CA), Cell Trace™ BODIPY® TR methyl ester, LysoTracker Red DND-99. In one embodiment, the compound is Calcein AM which is a non-fluorescent, cell permeant compound that is hydrolyzed by intracellular esterases into the fluorescent anion calcein, resulting in intact, live cells displaying bright green fluorescence, whereas cells without esterases, in particular dead, apoptotic and metabolically inactive cells, remain unstained.

The various types of differentiated colonies are described below. Erythroid progenitors [colony-forming unit-erythroid (CFU-E) and burst-forming unit-erythroid (BFU-E)] are detected by their ability to produce colonies of maturing erythroblasts in the presence of erythropoietin (EPO). The distinctive reddish color of the hemoglobin in erythroblasts of mature CFU-E and BFU-E colonies assists in their recognition. Myeloid progenitors [CFU-granulocyte (CFU-G), CFU-macrophage (CFU-M), and CFU-GM] produce colonies that contain 50 to several thousand granulocytes, macrophages or both cell types in the presence of one or more of the following cytokines-GM-colony stimulating factor (GM-CSF), Interleukin-3 (IL-3), IL-6, G-CSF, and Stem Cell Factor (SCF). Because of their primitive nature, CFU-GEMM tends to produce large colonies of >500 cells containing erythroblasts and recognizable cells of at least one other lineage. The use of an optimal combination of cytokines, that supports the differentiation of multiple lineages, allows the detection of CFU-E, BFU-E, CFU-GM and CFU-GEMM within the same culture. CFU-E-derived colonies are best detected using a magnification of 40-50.times. BFU-E, CFU-GM and CFU-GEMM can then be scored at the lower magnification and a higher magnification can be used to confirm colony type (if differentiated).

Modifications to culture medium that promote the proliferation of hematopoietic progenitors would facilitate the use of the CFC assay for clinical applications, making CFC assays faster and enabling counting of colonies after the shorter time. The proliferation of progenitor cells can be increased by using combinations of growth factors that are mitogenic for primitive multipotent progenitors and for more differentiated progenitors of individual lineages. Supraphysiologic concentrations of these factors can increase colony size by reducing the lag time between cell plating and initial cell division, decreasing the time between successive cell divisions and by promoting symmetric cell divisions that lead to cell expansion over asymmetric divisions that lead to differentiation and/or apoptosis.

Standard colony assays comprise components that support erythroid, myeloid and multipotent colonies that can be distinguished on the basis of morphological criteria after a culture period of, usually, 14-16 days. The present inventors have shown that it is possible to detect these colonies after much shorter culture periods, e.g. 5 to 10 days, but the colonies are much smaller and most cells are still undifferentiated. Culture media formulations can be prepared that accelerate the proliferation of progenitor cells and increase colony size after a shorter culture period. One such culture medium comprises FLT-3 Ligand (FL) and Thrombopoietin (TPO). In one embodiment, the culture medium further comprises components that selectively promote the growth of colonies of all types within the culture time period. In an embodiment, the culture medium further comprises combinations of hematopoietic growth factors or cytokines that promote proliferation of most types of progenitors. Such combination of factors include without limitation Stem Cell Factor (SCF), erythropoietin (EPO), Interleukin-3 (GM-CSF), Granulocyte/Macrophage Colony-Stimulating Factor (GM-CSF), G-CSF and/or Interleukin-6 (IL-6) that act on multipotent progenitors as well as on progenitors for erythroid, monocyte and macrophage progenitors.

Accordingly, in another embodiment, the modified culture medium further comprises cytokines, such as IL-3, IL-6, SCF, GM-CSF, G-CSF and/or EPO. In one embodiment, the cytokines are IL-3, IL-6, SCF, GM-CSF, G-CSF and EPO.

Typical concentration ranges of each individual cytokine are from 10 to 100 ng/mL. In one embodiment, the concentration ranges of each individual cytokine are from 20 to 50 ng/mL. In another embodiment, the concentration is 20 ng/mL for IL-3, IL-6, G-CSF and GM-CSF respectively, 50 ng/mL for SCF, TPO and FLT-3-Ligand, respectively, and 3 U/mL (corresponding to approximately 30 ng/mL) for EPO.

The culture media may also further comprise factors that promote cell metabolism and/or proliferation. Such factors include proteins, such as insulin, insulin-like growth factors and transferrin and metals, such as zinc. Accordingly, in an embodiment, the modified culture medium is supplemented with proteins or metals. In one embodiment, the protein is insulin, insulin-like growth factors or transferrin. In another embodiment, the metal is zinc, iron, copper or magnesium. In one embodiment, the metal is zinc, optionally, at a concentration of 2-20 μM. In another embodiment, the zinc concentration is 10-20 μM.

A preferred formulation contains Iscove's Modified Dulbecco's Medium, 0.8-1% methylcellulose, 1-2% pretested bovine serum albumin, 0-30% pretested fetal bovine serum, $1\times10^{-4}$ M 2-mercaptoethanol, 2 mM glutamine, 20 μM Zinc Sulfate and the cytokines SCF, IL-3, IL-6, GM-CSF, G-CSF and EPO. Another preferred formulation contains Iscove's Modified Dulbecco's Medium, 0.8-1% methylcellulose, 1-2% pretested bovine serum albumin, 0-30% pretested fetal bovine serum, $1\times10^{-4}$ M 2-mercaptoethanol, 2 mM glutamine, 10-20 μM Zinc Sulfate and the cytokines SCF, IL-3, IL-6, GM-CSF, G-CSF, FL, TPO and EPO.

Cell output per progenitor cell can be increased by uncoupling mitogenic actions of cytokines from actions that promote differentiation. This can be achieved with inhibitors of intracellular signalling molecules that mediate the differentiation-inducing actions of growth factors, but that are not necessary for mitogenesis. Accordingly, in another embodiment, the culture medium further comprises components to prevent differentiation and apoptosis of hematopoietic progenitors. Such components include inhibitors of cell signalling intermediates that are involved in terminal differentiation and apoptosis of hematopoietic cells. Examples include, without limitation, steroid hormones, such as dexamethasone, peptides of the renin-angiotensin system and inhibitors of Caspase, Fas and proapoptotic Bcl-2 family members.

Applications that require a faster CFC assay include the evaluation of graft quality and potency after cryopreservation to determine its suitability for transplantation. It has been shown that the post-thaw numbers of CFCs in cryopreserved cord blood units are a strong independent predictor of neutrophil and platelet engraftment after umbilical cord blood transplants (UCBT) (Prasad et al. Blood (2008)). Transplantation with cord blood units containing CFC numbers of $5.6\times10^4$ or more per kg body weight has been shown to result in shorter time to neutrophil and platelet engraftment than transplantation with cord blood units containing fewer CFC numbers (Prasad et al. Blood (2008)). The standard 14-16 days culture period of a standard CFC assay is typically too long to use the CFC-assay prospectively to evaluate the suitability of a cell preparation, for example, cord blood units, for transplantation, as usually only 1 to 2 weeks are available between identification of the candidate CB units in a CB bank and the start of transplantation procedures.

Accordingly, in another aspect, the disclosure provides a method of predicting or evaluating the quality of hematopoietic grafts prior to transplantation using the methods described herein. The term "predicting or evaluating the quality of hematopoietic grafts" includes, without limitation, comparing the numbers of CFUs in a sample to a known positive or negative control to assess the suitability or quality of the graft for transplantation.

The term "control" includes any predetermined value or sample that can be used to establish a base value for a good quality graft (positive control) or a poor quality graft (negative control). The predetermined value may be established by testing control samples and establishing a known value. In such an embodiment, use of a control sample is not required for each test.

The term "hematopoietic graft" as used herein refers to the transfer of hematopoietic cells or tissue to a subject in need thereof. Such grafts, include without limitation, bone marrow (BM), cord blood (CB) and mobilised peripheral blood (MPB) samples for transplantation. The graft may be allogeneic, where the sample is transferred from one subject to another subject; xenogeneic, where the sample is transferred from a foreign species; syngeneic, wherein the sample is from a genetically identical donor or an autograft, where the sample is transferred from one site to another site on the same subject.

The term "subject" includes all members of the animal kingdom, including human. In one embodiment, the subject is an animal. In another embodiment, the subject is human.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Preparation of a Hematopoietic CFC Assay

Frozen ficolled cord blood mononuclear cells were thawed, nucleated cells were counted by microscopy using a hemacytometer after dilution in 3% acetic acid to lyse mature erythrocytes. The cells were diluted with Iscove's MDM to 10-fold the desired cell concentration. 0.4 mL of the cell suspensions were added into an aliquot of test MethoCult® medium (4 mL) and mixed by vortexing. 1.1 mL of each cell/medium mixture was dispensed into triplicate 35 mm culture dishes using 3 mL syringes with blunt end needles, with 1.1 mL of medium per dish. All cultures were incubated for 4, 7, 10 or the standard 14 days at 37.degree. C., 5% $CO_2$, 100% humidity. Colonies were enumerated and classified by bright-field microscopy into the following categories based on size and morphology: CFU-E, BFU-E, CFU-GM, CFU-GEMM (StemCell Technologies, Colony Atlas).

Example 2

Comparison of 4 Different Methocult® Media

Figure 1:
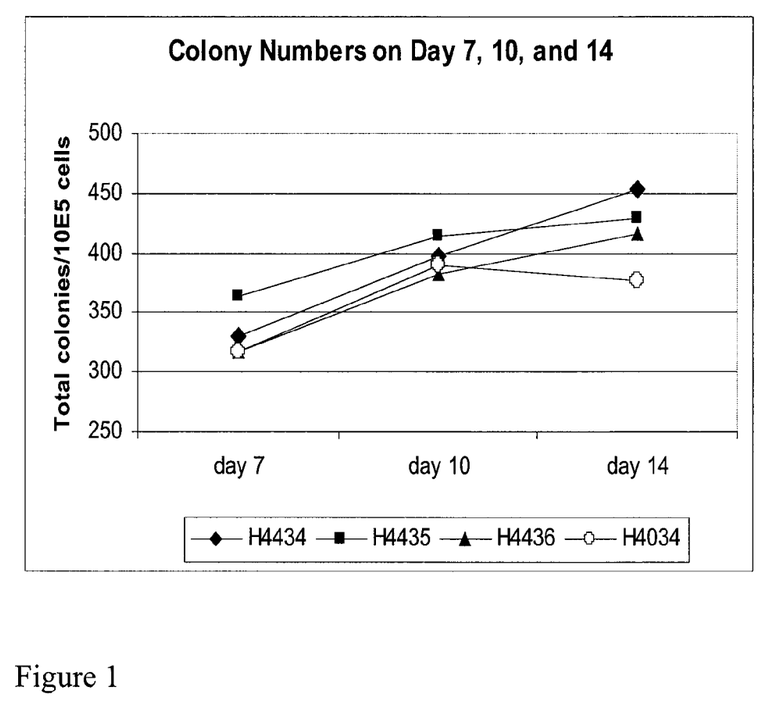
FIG. 1 shows the total colony numbers of a colony assay on Cord Blood (CB) mononuclear cell cultures in 4 different MethoCult® media. Colonies were enumerated after 7, 10 and the standard 14 days of culture.

Human CB mononuclear cells were suspended in 4 different methylcellulose-based culture media containing cytokines (MethoCult®. H4434, H4435, H4436, H4034) (StemCell Technologies 2008 Catalog, p 186, 190) at a concentration of $1\times10^4$ cells per 1.1 mL of medium and cultured as described in Example 1. On day 4, no colonies were detectable in all culture dishes, indicating 4-day incubation was not enough for progenitors to form colonies in any of the media. On day 7, small (minimum 20 cells per colony) to intermediate size colonies were seen in all four media. As shown in FIG. 1 total colony numbers were increased in all media tested on day 10 when compared to day 7. Comparing colonies among four different MethoCults, more and relatively bigger colonies grew in H4435 than in the other media (FIG. 1). On day 7 all colonies were morphologically immature and erythroid (BFU-E), myeloid (CFU-GM) and multilineage colonies could not be distinguished. On day 10, some erythroid colonies were detectable based on the morphology, but they were not fully differentiated. On day 14, erythroid colonies showed mature structure and hemoglobinization. Both BFU-E and CFU-GM were easy to distinguish, according to standard scoring criteria (StemCell Technologies, Colony atlas). For total colony numbers, an increase was seen in H4434, H4435 and H4436 but not in H4034 on day 14 when compared to day 10. Thus, the present inventors concluded that H4435 was the best formulation among the four Media for detecting and enumerating colonies after a shorter culture period.

Example 3

Comparison of Total Colony Numbers at 7 and 14 Days of Culture

Figure 2:
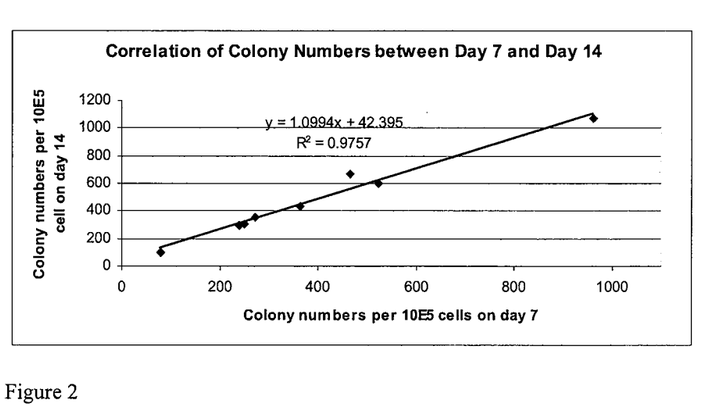
FIG. 2 shows the correlation between colony numbers on day 7 and day 14 for 10 different Cord Blood samples cultured in Methocult® H4435 medium.

To determine whether colony numbers on day 7 are representative of colony numbers after a standard 14-day culture period in H4435 medium, ten experiments were performed with CB from 9 donors. Colonies were evaluated on day 7 and day 14 by one person to maintain consistency. Results showed that total colony numbers on day 7 were significantly lower than those on day 14 ($P<0.05$). Average colony numbers on day 7 to day 14 were 81±6% (Table 1). However, the correlation of the colony numbers between day 7 and day 14 was statistically significant ($P<0.0001$, Pearson test), indicating that colony numbers on day 7 are proportional to those on day 14 (FIG. 2).

Example 4

Difference in Colony Size Between Day 7 and Day 14

Figure 3:
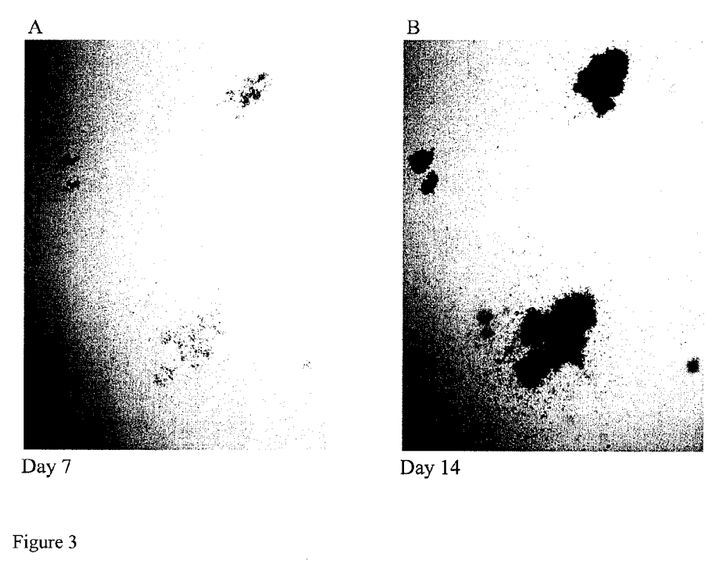
FIG. 3 shows photographs of the same hematopoietic colonies after 7 days (A) and 14 days (B) of culture of CB mononuclear cells in MethoCult® H4435 medium. Colonies were photographed using a 2.5× objective.

Colonies grown from CB mononuclear cells were photographed after 7 and again after 14 days of culture. Colony morphology on day 7 appeared as small cell clusters with fewer cells compared to day 14 (FIG. 3). The cells in the colonies were typically small and round on day 7. It was not possible to distinguish erythroid and myeloid colonies after 7 days as the cells were morphologically immature. The colonies, however, fulfilled the characteristics of traditional CFU description, i.e., a cell cluster or group of cell clusters with a minimum of 20 cells per colony.

Example 5

Figure 4:
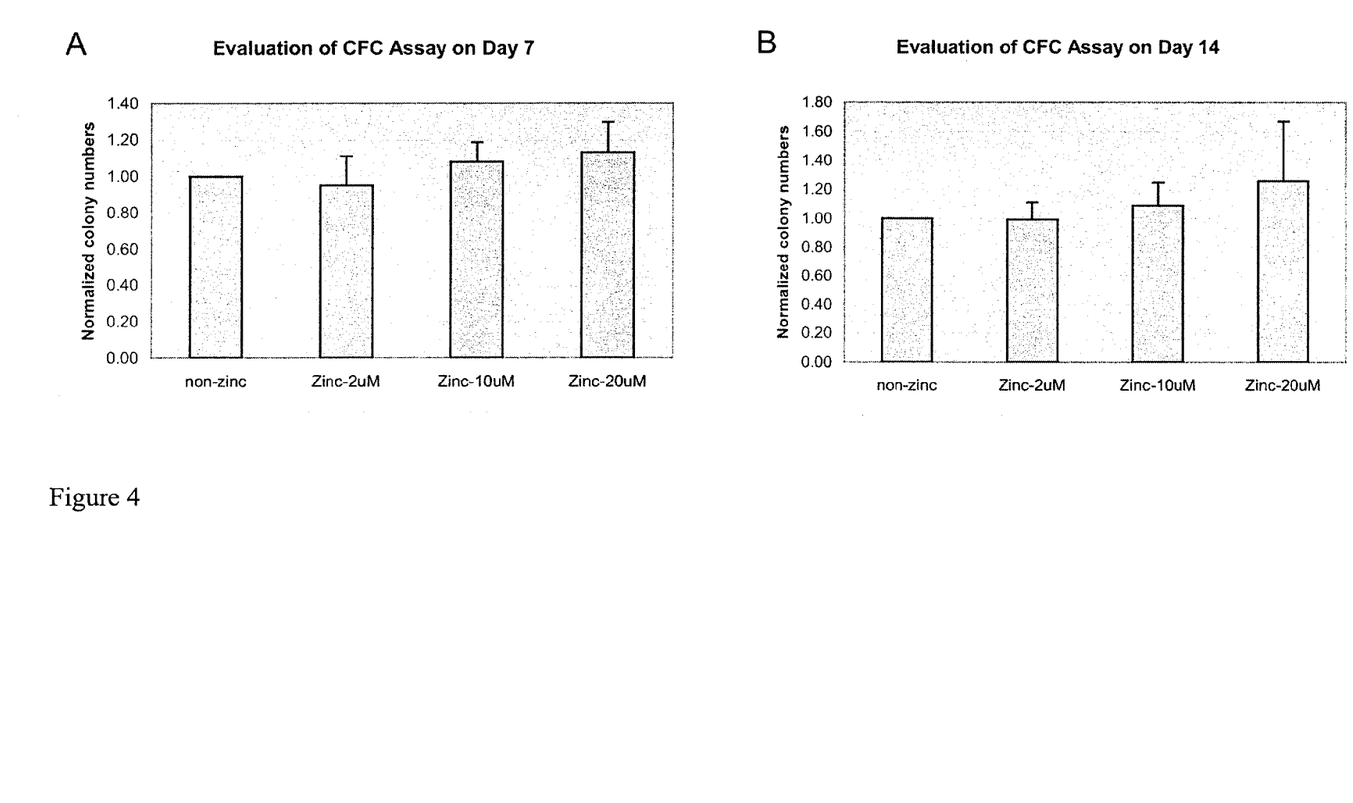
FIG. 4 shows the effect of Zinc on total colony numbers after 7 days (A) and 14 days (B) of culture. Results are expressed as average+/−standard deviations for 4 experiments, with CB cells from 4 different donors. Colony numbers are normalized to colony numbers in the absence of zinc.

Increase of Colony Numbers and Size in MethoCult® Medium Supplemented with Zinc Sulphate Methocult® H4435 medium, which contains the 6 cytokines IL-3, IL-6, SCF, GM-CSF, G-CSF and EPO, was supplemented with Zinc Sulphate at final concentrations 2, 10 and 20 µM and 4 different CB samples were cultured for 7 and 14 days as described in Example 1. The morphology of the colonies on day 7 showed noticeable differences between zinc-free and -containing conditions in three experiments. In zinc-containing medium, particularly at 10 and 20 uM, the colonies were larger, and more evenly spread out when compared to zinc-free medium. In one of the 4 experiments no effect of zinc-containing medium on colony size was seen after 7 days of culture, indicating that the effect of zinc on colony size may be donor-dependent. When colonies were evaluated after 14 days of culture no effects of zinc on colony size was observed in 3 of the 4 experiments. In one experiment, CFU-GM colonies were larger in the presence of zinc, whereas BFU-E colony size was unchanged. Further analysis demonstrated that total colony numbers on day 7 and 14 were increased in media containing 10 or 20 µM of Zinc relative to media containing no Zinc, or 2 µM of Zinc (FIG. 4).

Example 6

Proportionality of Colony Numbers

Figure 5A:
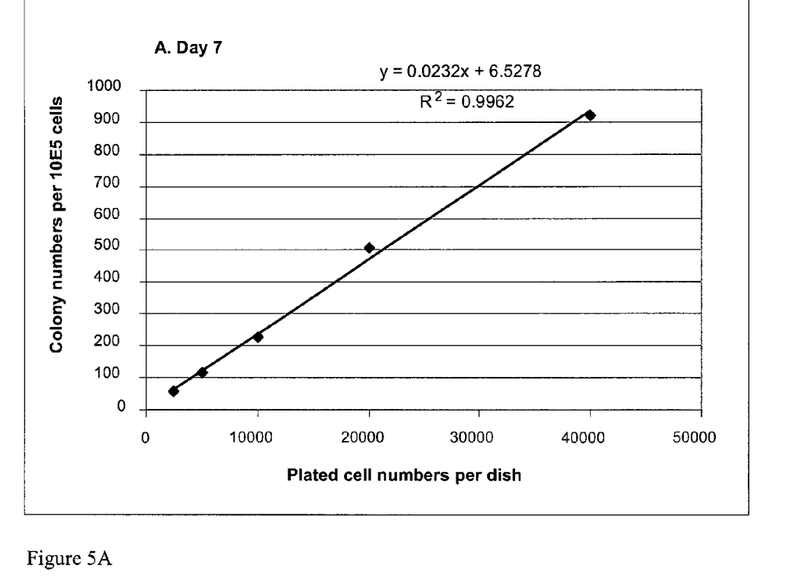
FIG. 5 shows the linear relationship between Cell numbers per dish and total colony numbers after 7 days (A) or 14 days (B) of culture. (C) Linear relationship between colony numbers on days 7 and 14.
Figure 5B:
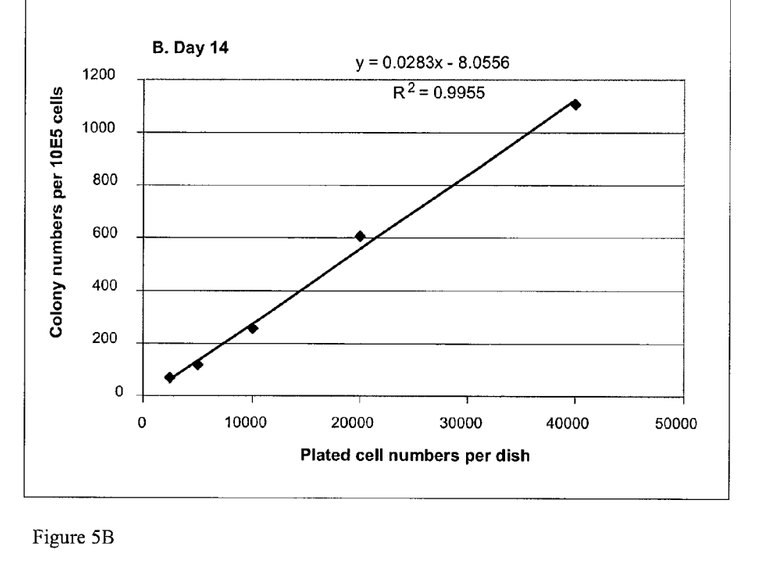
Figure 5C:
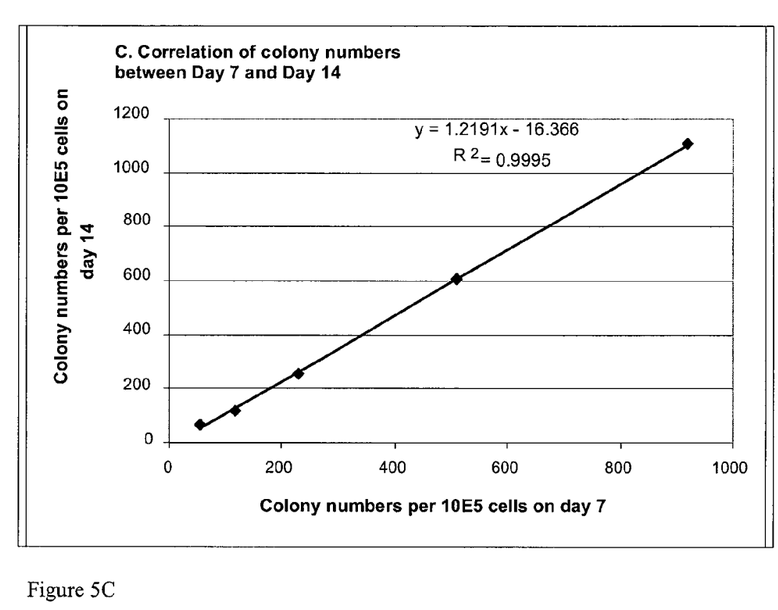

To examine whether colony numbers were proportional to cell numbers plated, mononuclear cord blood cells were plated at cell densities ranging from 2,500 to 40,000 per dish in MethoCult® H4435 medium, supplemented with 20 uM Zinc sulfate. Colony numbers and the numbers of cells plated per dish showed a linear relationship on day 7 and day 14 (FIG. 5). Comparison of colony numbers between day 7 and day 14 revealed a significant correlation in this range of cell densities, indicating that colony numbers at day 7 were representative of colony numbers at day 14 (FIG. 5C).

Example 7

Detection of Colonies by Staining with Calcein AM and Fluorescence Microscopy

Figure 6:
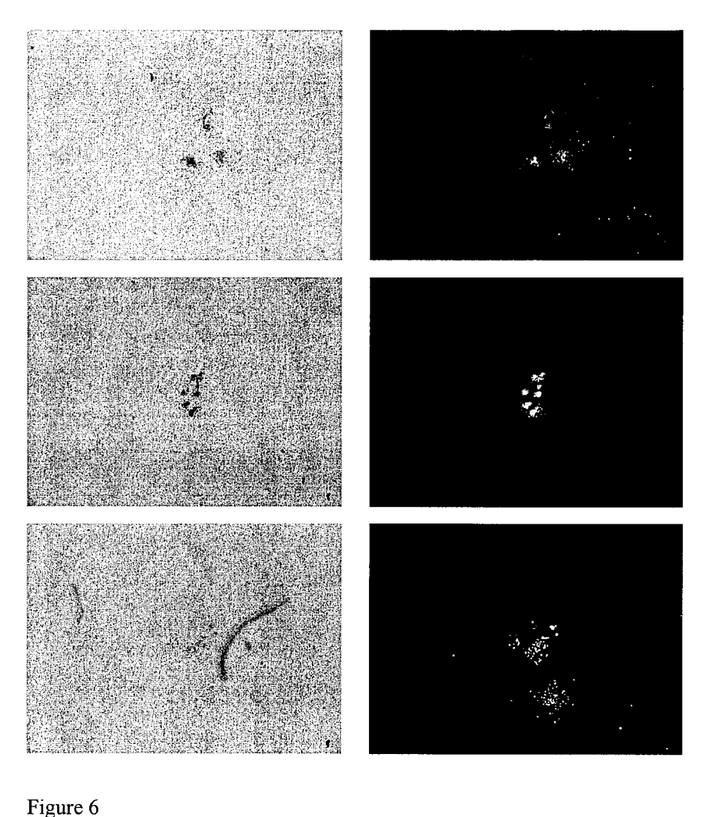
FIG. 6 shows photographs of hematopoietic colonies after 7 days of culture and 1-1.5 hour exposure to a cell labeling reagent, Calcein AM. Colonies were photographed using a 2.5× objective on an inverted fluorescence microscope. Bright field images (Left) were obtained after ¹⁄₄s s; exposure while fluorescence images (Right) were obtained using a FITC filter set and 4 s exposure times.

To examine whether a cell labelling reagent can be used to detect colonies in 7 days cultures, mononuclear cord blood were cultured in MethoCult® medium, supplemented with 20 uM Zinc sulfate. After culture, the dishes were overlaid with 200 µM of a solution of 0.5 µM Calcein AM (Invitrogen-Molecular Probes, Eugene, Oreg.) in phosphate buffered saline and incubated for a period of 1 to 1.5 hours at 37° C. before acquiring bright field and fluorescent images using a Leica DMIL inverted fluorescence microscope equipped with a Fuji SLR digital camera. Calcein AM is a non-fluorescent, cell permeant compound that is hydrolyzed by intracellular esterases into the fluorescent anion calcein, resulting in live cells displaying bright green fluorescence. As shown in FIG. 6, all colonies that were detectable by bright field microscopy (images on left side) became brightly fluorescent after exposure to the Calcein AM reagent and became detectable by fluorescence microscopy with very low background fluorescence (images on right side of FIG. 6). These results demonstrate that colonies in 7-day colony assays can be labeled with a cell labeling reagent and detected by fluorescence microscopy.

Example 8

Effect of Extra Cytokines on Colony Growth

To examine if adding extra cytokines can further increase colony growth, culture medium as in Example 5 was supplemented with FL, TPO or both. Cultures were set up using Cord Blood cells and colonies were counted after 7 and 14 days. Results of 4 experiments are shown in Table 2. Adding TPO and/or FL to the 6 cytokines used in Example 5 increased the number of colonies that were detectable after 7 days of culture of three of the four CB samples, but did not consistently change the numbers of colonies that were detectable after 14 days of culture. After 7 days of culture, colonies were consistently larger in cultures containing FL and TPO, compared to cultures without FL, TPO or both. In three of the four experiments colony size and morphology after 14 days were very similar whether or not TPO and/or FL were present in the medium. In one experiment (Exp 4 in Table 2) colonies were slightly larger in cultures without TPO and FL compared to cultures with TPO and FL. These results demonstrate that adding FL and TPO further improves colony size and morphology after the shorter 7 days culture period, but has little effect on colony growth after the regular 14 days culture period.

Example 9

Figure 7:
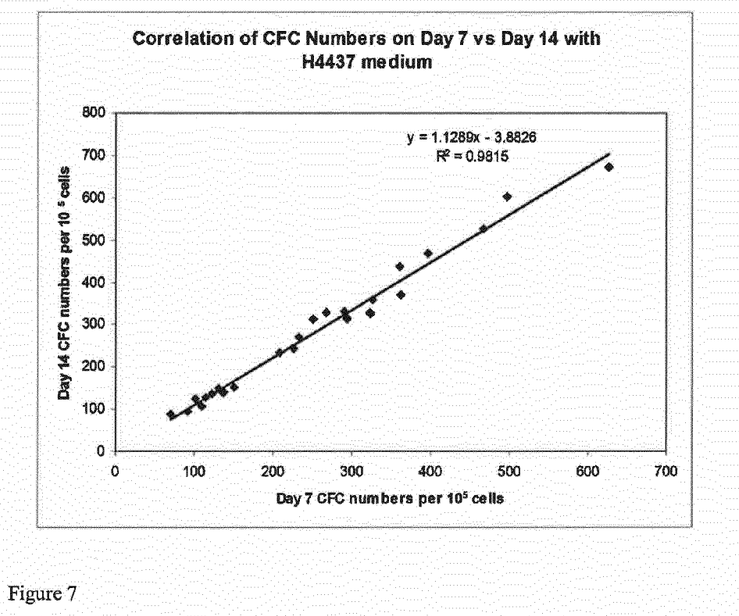
FIG. 7 shows the correlation between colony numbers on day 7 and day 14 for 27 different Cord Blood samples cultured in Methocult® H4435, supplemented with Zinc, FL and TPO.
Figure 8:
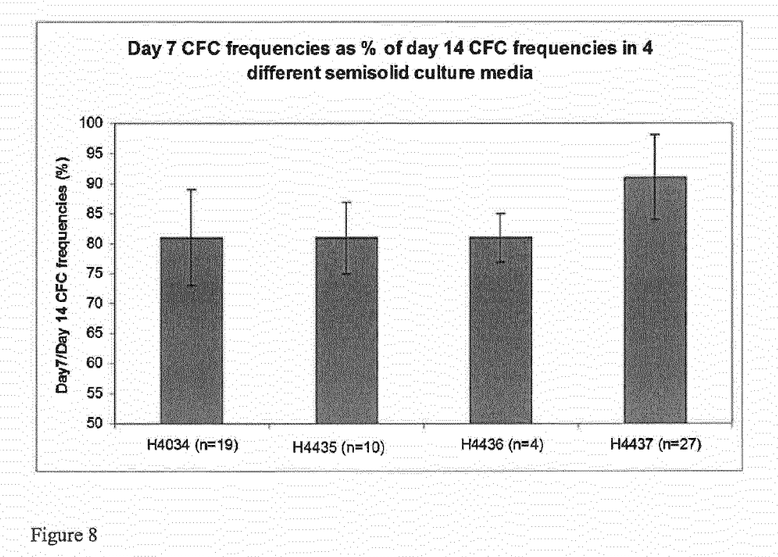
FIG. 8 shows the day 7 colony numbers expressed as percentage of the day 14 colony numbers obtained in colony assays on a number of different CB samples in 4 different Methocult® media.

Comparison of Total Colony Numbers at 7 and 14 Days of Culture in Medium with Zinc and 8 Cytokines To determine whether colony numbers on day 7 are representative of colony numbers after a standard 14-day culture period in the medium supplemented with Zinc, FL and TPO as in Example 8, designated as H4437 medium in FIGS. 7 and 8, cultures were performed with cells of 27 different CB samples and colonies were counted on days 7 and 14 as described in Example 3. The results, presented in FIG. 7, showed that colony numbers on day 7 and day 14 were significantly correlated ($P<0.0001$, Pearson test). Colony numbers on day 7 were on average 91% of colony numbers on day 14. (FIG. 8), which was 10% higher than the percentages of day 14 colonies that were detectable after 7 day of culture in the other media (FIG. 8). The differences between the results with the H4437 medium and the other media were statistically significant ($p<0.05$ for H4436 medium, $p<0.001$ for H4034, H4435 and H4436 media, t-test). With the H4437 medium colonies were already detectable after 5 days of culture, but day 5 colony numbers were less than 50% of day 7 colony numbers. These results demonstrated that culture in the H4437 medium allowed early detection of a much larger proportion of colony-forming cells than culture in the other media.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Total Colony Numbers after 7 and 14 days for 10 different experiments with CB MNC preparations from 9 different donors cultured in Methocult ® H4435 medium

| Exp # | Day 7 | day 14 | Day 7/14 (%) |
|---|---|---|---|
| 1 | 363 | 430 | 84 |
| 2 | 330 | 395 | 84 |
| 3 | 80 | 100 | 80 |
| 4 | 273 | 350 | 78 |
| 5 | 523 | 597 | 88 |
| 6 | 963 | 1070 | 90 |
| 7 | 240 | 293 | 82 |
| 8 | 467 | 667 | 70 |
| 9 | 252 | 308 | 82 |
| 10 | 353 | 450 | 79 |
| AVE | 385 | 466 | 81 |
| STDEV | 238 | 266 | 6 |

TABLE 2

Effect of adding TPO and FL to MethoCult medium on colony growth of hematopoietic progenitors in cord blood

| Cytokines: IL-3, IL-6, G-CSF, GM-CSF, SCF, EPO | Exp. 1[1] | %[2] | Size, Morphology ranking[3] | Exp. 2[1] | %[2] | Size, Morphology ranking[3] | Exp. 3[1] | %[2] | Size, Morphology ranking[3] | Exp. 4[1] | %[2] | Size, Morphology ranking[3] | %[2] Average | SD |
|---|---|---|---|---|---|---|---|---|---|---|---|---|---|---|
| 7 days | | | | | | | | | | | | | | |
| no extra cytokines | 270 | | 3 | 387 | | 3 | 297 | | 4 | 343 | | 2 | | |
| with TPO | 210 | 78 | 2 | 393 | 102 | 1 | 317 | 107 | 2 | ND | | | 95 | 15 |
| with FL | 267 | 99 | 2 | 413 | 107 | 2 | 293 | 99 | 3 | ND | | | 101 | 5 |
| with FL and TPO | 250 | 93 | 1 | 397 | 103 | 1 | 327 | 110 | 1 | 360 | 105 | 1 | 103 | 9 |
| 14 days | | | | | | | | | | | | | | |
| no extra cytokines | 307 | | 1 | 470 | | 1 | 337 | | 1 | 477 | | 1 | | |
| with TPO | 287 | 93 | 1 | 480 | 102 | 1 | 360 | 107 | 1 | ND | | | 101 | 7 |
| with FL | 337 | 110 | 1 | 463 | 99 | 1 | 317 | 94 | 1 | ND | | | 101 | 8 |
| with FL and TPO | 313 | 102 | 1 | 467 | 99 | 1 | 360 | 107 | 1 | 370 | 78 | 2 | 96 | 4 |

[1]Colony numbers per $10^5$ cells plated
[2]Colony numbers as percentage of colony numbers in medium without extra cytokines
[3]Ranking on the basis of colony size and morphology: 1 is best, 4 is worst.

REFERENCES

1. Bacigalupo A, Piaggio G, Podesta M et al. Influence of marrow CFU-GM content on engraftment and survival after allogeneic bone marrow transplantation. Bone Marrow Transplantation: 15, 221-226, 1995
2. Torres A, Alonso M C, Gomez-Villagran J L et al. No influence of number of donor CFU-GM on granulocyte recovery in bone marrow transplantation for acute leukemia. Blut 50: 89-94, 1985

3. Burger S R, Kadidlo D and McCullough J. Improved progenitor assay standardization using peripheral blood mononuclear cells from a donor treated with granulocyte-colony stimulating factor. Transfusion 39: 451-456, 1999
4. Lumley M A, Burgess R, Billingham L J et al. Colony counting is a major source of variation in CFU-GM results between centres. British Journal of Haematology 97: 481-484, 1997
5. Lamana M, Albella B, Rodriguez F et al. Conclusion of a national multicenter incomparative study of in vitro cultures of human hematopoietic progenitors. Bone Marrow Transplantation 23: 373-380, 1999
6. Prasad V K, Mendizabal A, Parikh S H et al Unrelated donor umbilical cord blood transplantation for inherited metabolic disorders in 159 pediatric patients from a single center: influence of cellular composition of the graft on transplant outcomes. Blood. 2008 Jun. 27. [Epub ahead of print]
7. StemCell Technologies Colony Atlas
8. StemCell Technologies Methocult® Flyer
9. StemCell Technologies 2008 Catalog, pp. 186, 190.

The invention claimed is:

1. A method of determining the number of hematopoietic colony forming cells in a starting cell preparation comprising:
   a) culturing the cell preparation for 7-10 days in a semi-solid culture medium comprising FLT-3 Ligand (FL) and Thrombopoietin (TPO);
   b) detecting and enumerating the colonies; and
   c) assessing the number of colony forming cells in the starting cell preparation based on the number of colonies in step (b); wherein the number of colonies in step (b) is at least 80% of the number of colonies derived from the same colony forming cells when measured on day 14; wherein the starting cell preparation comprises hematopoietic tissue or cells selected from blood, bone marrow, cord blood, placenta, spleen, fetal liver, yolk sac and aorta-gonad-mesonephros region or wherein the starting cell population comprises embryonic stem cell lines or induced pluripotent stem cells lines.

2. The method of claim 1, wherein the number of colonies in step (b) is at least 90% of the number of colonies when measured on day 14.

3. The method of claim 1, wherein enumeration is performed by an automated colony detection instrument.

4. The method of claim 1, wherein the culture period is from 7-8 days.

5. The method of claim 4, wherein the culture period is 7 days.

6. The method of claim 1, wherein the semi-solid culture medium comprises a semi-solid medium selected from a methylcellulose, agar, collagen and plasma clot based culture medium.

7. The method of claim 6, wherein the semi-solid medium is methylcellulose based.

8. The method of claim 1, wherein the hematopoietic tissue or cells comprise bone marrow, cord blood or mobilized peripheral blood.

9. The method of claim 1, wherein the starting cell preparation has been cryopreserved.

10. The method of claim 1, wherein the culture medium comprises one or more further cytokines selected from IL-3, IL-6, SCF, GM-CSF, G-CSF and EPO.

11. The method of claim 1, wherein the culture medium is supplemented with a protein or metal that accelerates colony formation by hematopoietic progenitors.

12. The method of claim 11, wherein the protein is insulin, insulin-like growth factor or transferrin.

13. The method of claim 11, wherein the metal is zinc.

14. The method of claim 13, wherein the zinc is added to the culture medium in a concentration of 2-20 $\mu M$.

15. The method of claim 14, wherein the zinc is added to the culture medium in a concentration of 10-20 $\mu M$.

16. A method of predicting or evaluating the quality of a hematopoietic graft comprising measuring the number of hematopoietic colony forming cells in a starting cell preparation derived from the hematopoietic graft using the method of claim 1; wherein the number of the hematopoietic colony forming cells in the starting cell population is indicative of the quality of the hematopoietic graft.

17. The method of claim 16, wherein the graft is allogeneic, xenogeneic, syngeneic or autologous to a subject in need thereof.

18. The method of claim 17, wherein the subject is human.

* * * * *